United States Patent [19]

Duncan et al.

[11] Patent Number: 4,535,818

[45] Date of Patent: Aug. 20, 1985

[54] VALVE ASSEMBLY

[75] Inventors: Richard K. Duncan; Norton A. Russell, both of Yellow Springs, Ohio

[73] Assignee: Vernay Laboratories, Inc., Yellow Springs, Ohio

[21] Appl. No.: 536,108

[22] Filed: Sep. 26, 1983

[51] Int. Cl.³ ............................................. F16K 15/14
[52] U.S. Cl. .................................. 137/846; 137/850; 604/122; 604/247
[58] Field of Search ....................... 137/846, 847, 850; 604/83, 86, 122, 247

[56] References Cited

U.S. PATENT DOCUMENTS

| | | | |
|---|---|---|---|
| 568,669 | 9/1896 | Ellsworth | 137/846 X |
| 2,948,297 | 8/1960 | Langdon | 137/846 |
| 3,822,720 | 7/1974 | Souza . | |
| 3,837,381 | 9/1974 | Arroyo | 137/846 X |
| 3,886,937 | 6/1975 | Bobo | 137/850 X |
| 3,901,272 | 8/1975 | Banners et al. . | |
| 3,933,282 | 1/1976 | Stevens | 137/846 X |
| 4,038,983 | 8/1977 | Mittleman | 604/124 |
| 4,341,239 | 7/1982 | Atkinson . | |
| 4,436,519 | 3/1984 | O'Neill | 137/847 X |

Primary Examiner—Robert G. Nilson
Attorney, Agent, or Firm—Biebel, French & Nauman

[57] ABSTRACT

A valve assembly for permitting relatively free flow in a first direction and for preventing flow in a second, opposite direction in a flow path includes a housing having first and second ports and defining a housing interior having an interior surface. A resilient flow regulator includes a pair of lips arranged in a converging relationship to define for the regulator an open end and a normally closed end. At the normally closed end, the lips are disposed adjacent each other to define a normally closed slit therebetween, and to define inner and outer surfaces for the lips. The regulator further includes at least one side wall interconnecting the lips. The regulator is secured within the housing interior so that flow in the first direction is from the first port, through the open end, through the normally closed end, and to the second port. The housing interior defines a shape such that the regulator is secured therein by the securing means with the outer surface of each of the lips being substantially adjacent to the housing interior surface.

7 Claims, 22 Drawing Figures

FIG-1
FIG-2 PRIOR ART
FIG-3 PRIOR ART
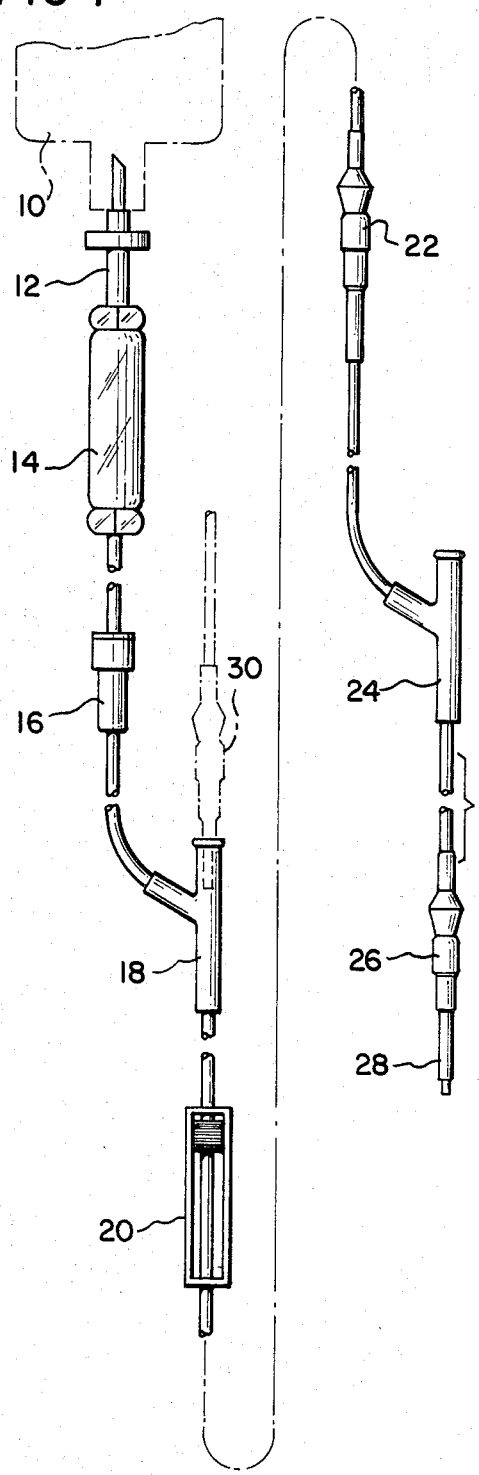
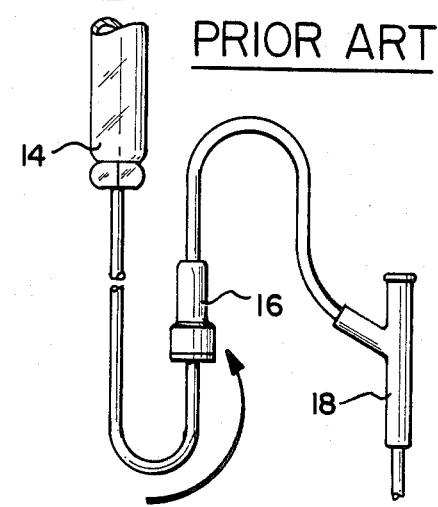
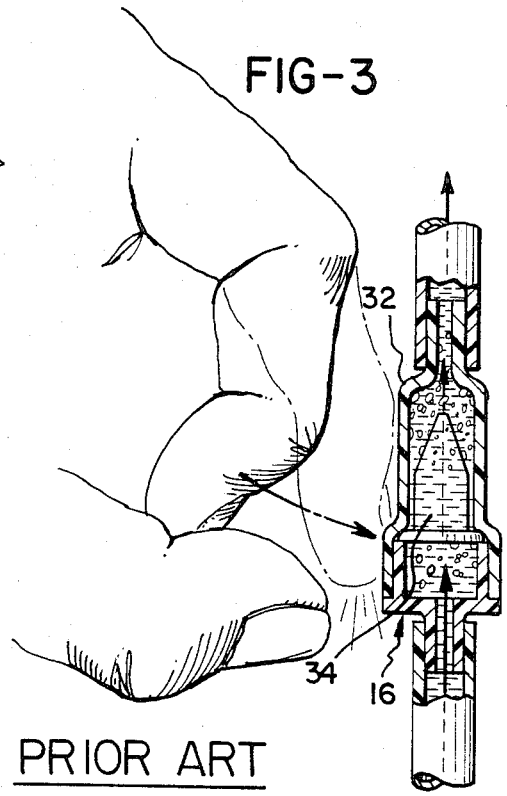

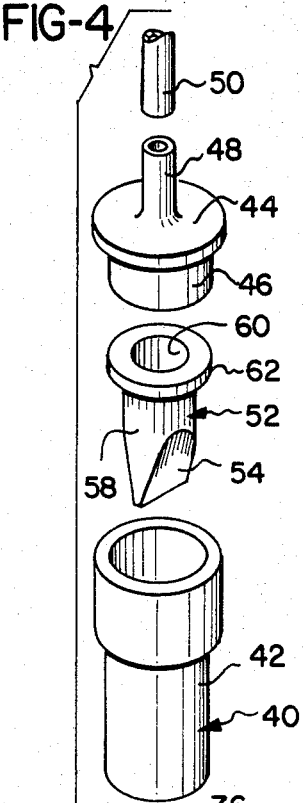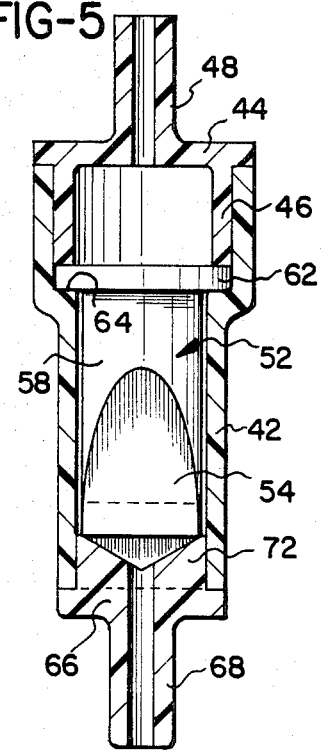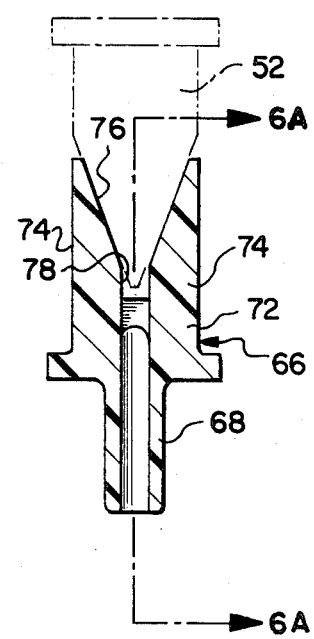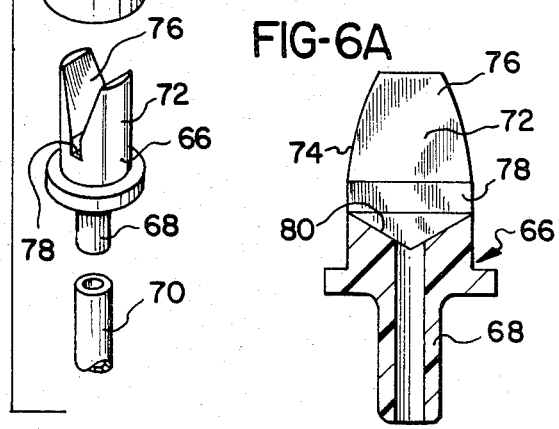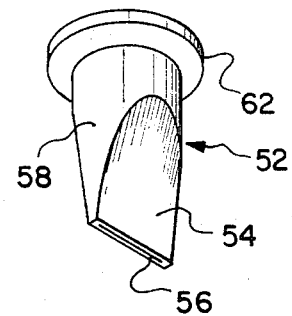

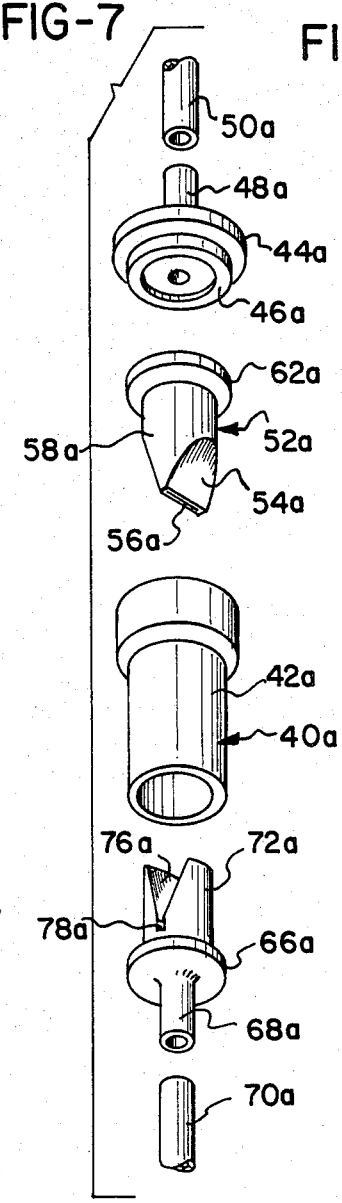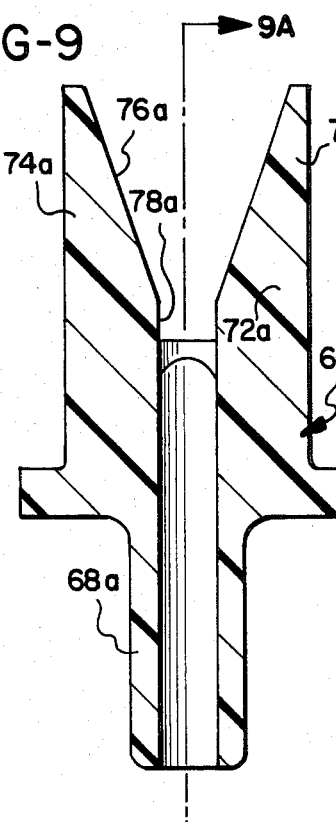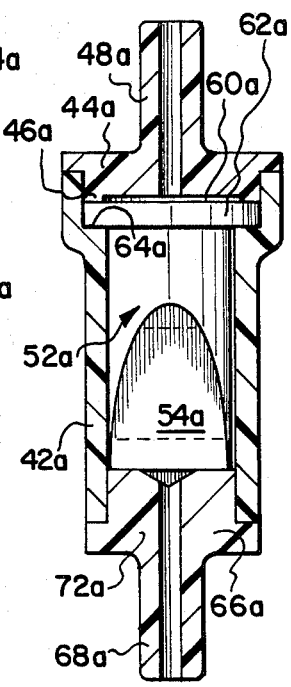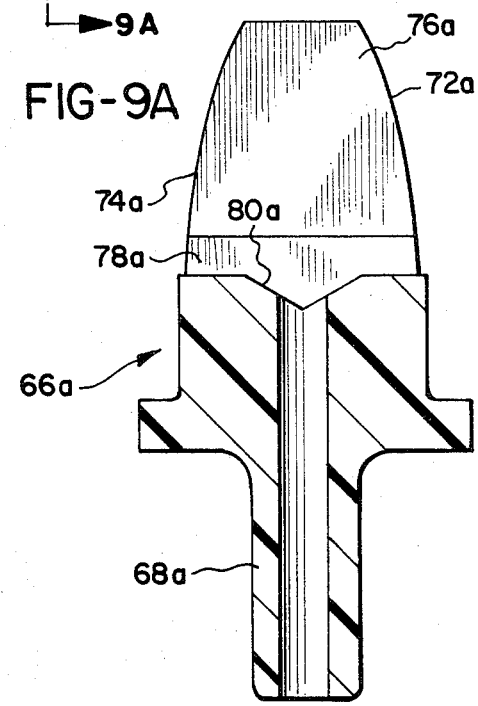

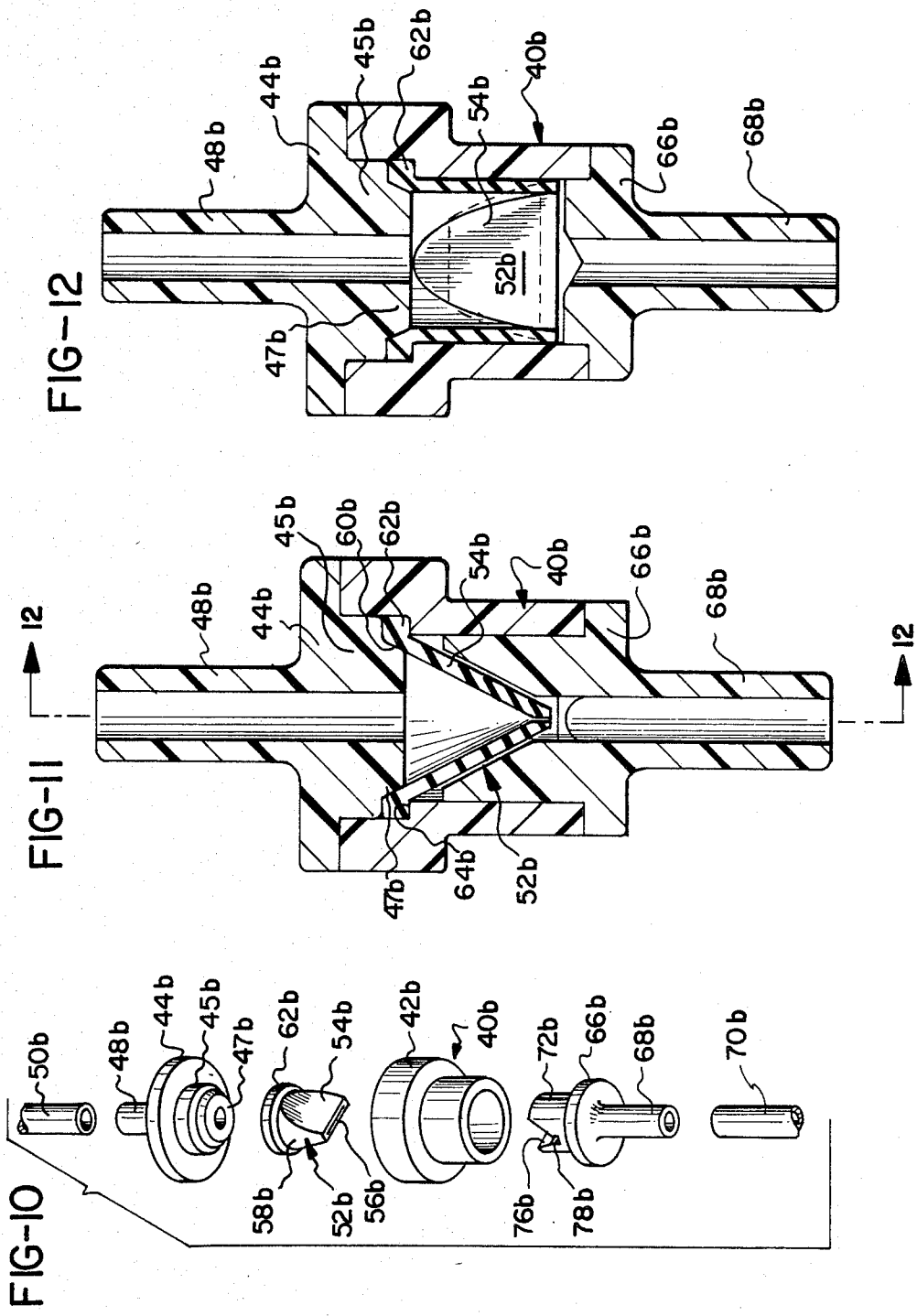

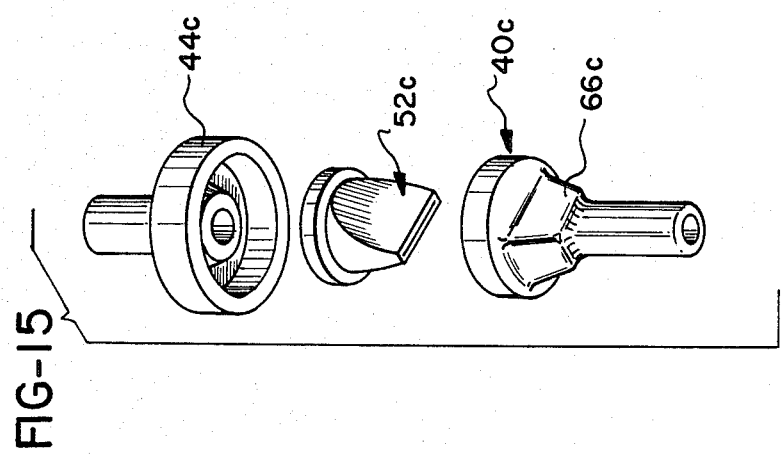
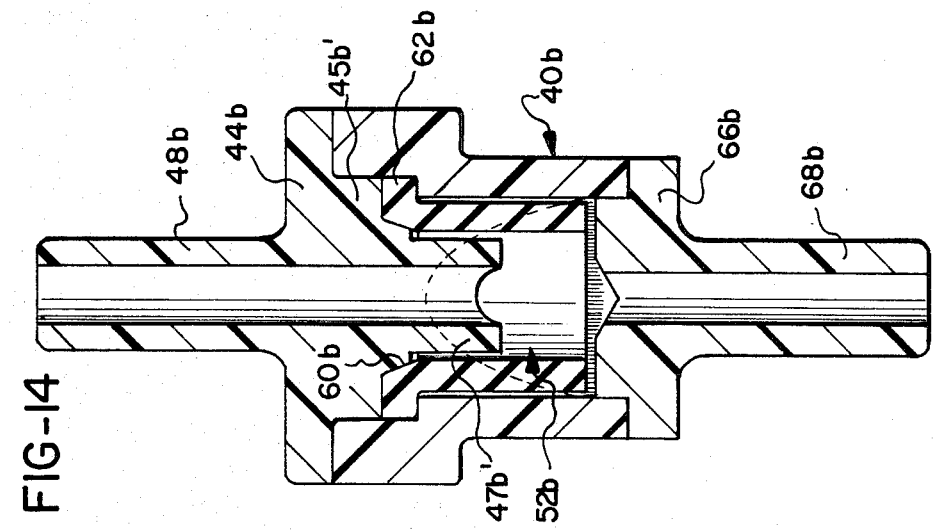
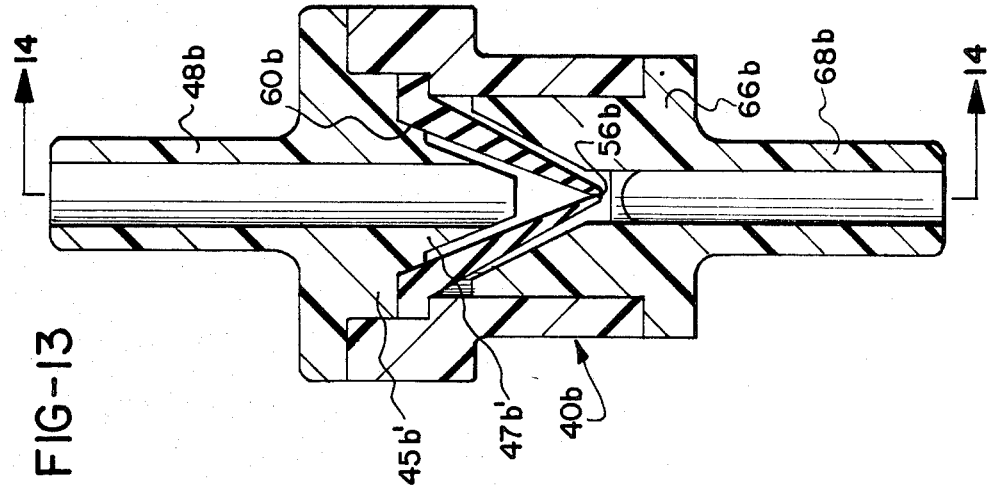

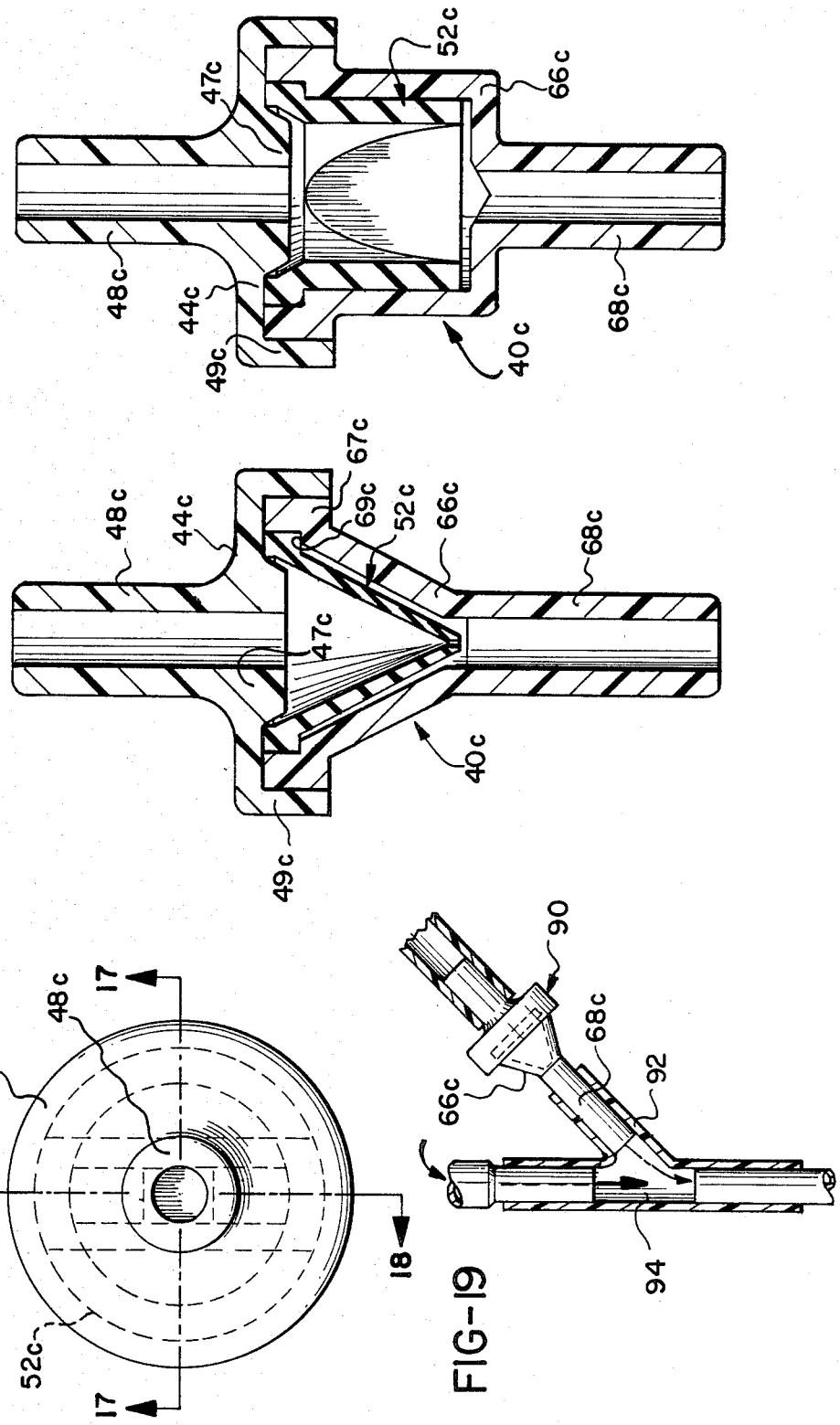

VALVE ASSEMBLY

BACKGROUND OF THE INVENTION

The present invention relates generally to flow regulation apparatus, and more particularly, to a valve assembly adapted to permit substantially free flow through the valve in a first direction, while preventing flow through the valve in a second, opposite direction. Even more particularly, the present invention relates to valves commonly known as the "duck-bill" type.

Duck-bill valves have been known for some time and have been used in a variety of applications, several examples being shown in U.S. Pat. Nos. 3,822,720 and 3,901,272. Such a valve typically includes a housing into which is mounted a resilient flow regulator member having as its primary operative components a pair of lips arranged in a converging relationship from an open end to a normally closed end. At the normally closed end of the regulator, the lips are located adjacent each other so as to define a normally closed slit therebetween. The regulator is mounted within the housing in a sealed relationship so that flow through the housing must pass through the regulator as well. In a first or forward direction, flow enters the housing and passes into the regulator through the open end, moving toward the normally closed end. The flow pressure against the resilient lips opens the slit, allowing the flow to pass out of the regulator and the housing. When flow enters the housing from a second or reverse direction, however, flow contacts the regulator at its normally closed end, with the flow pressure against the resilient lips holding the slit in its closed position, thereby preventing flow through the valve assembly.

One application for a valve of this type is as part of a medical solution administration set. Such a set is used to deliver fluids such as plasma, medicines, and the like from a fluid supply source, such as a bottle or bag, intraveneously to a patient. A typical administration set is shown in the accompanying drawings as FIG. 1.

A fluid supply 10 is coupled by connector 12 to a drip chamber 14. Fluid then passes through duck-bill check valve assembly 16 and to one leg of a Y-site 18. The fluid next passes through an adjustable clamp 20, a filter and manual pump device 22, a second Y-site 24, and a second filter and manual pump device 26. An adapter 28 is provided at the lower end of the fluid path for connection to a needle (not shown) which is inserted into a vein of the patient.

The valve assembly 16 is placed within the fluid path so that downward flow through valve assembly 16 is in the forward direction of the valve, thereby permitting fluid to flow downwardly from supply 10 to the patient.

Occasionally, it will be necessary to provide the patient with medicine or some fluid other than that provided from supply 10. To avoid having to disconnect supply 10 from the administration set, and to provide a continuous flow of fluid to the patient, the second fluid is introduced to the administration set through filter, manual pump and adapter device 30 at Y-site 18. The second fluid supply source (not shown) is suspended at an elevation higher than supply 10. Fluid from the second source thus is at a greater fluid pressure than that from supply 10, and the second fluid displaces the first fluid at Y-site 18 and flows downwardly to the patient. Fluid from the second source will also travel upwardly toward source 10 from Y-site 18, but will be prevented from contaminating the first fluid through the action of valve assembly 16.

Whenever fluid flow is commenced through the administration set, such as when it is initially connected to fluid source 10, air bubbles typically collect around valve assembly 16. Once fluid flow is established, these bubbles must be carried away with the fluid flow, so that they will not obstruct or interfere with the smooth flow of fluid through the administration set at a constant rate.

When a duck-bill valve of the type known heretofore is used, it is necessary to dislodge the bubbles from the valve assembly 16 for them to be carried away by the fluid stream. This requires initially grasping the valve assembly 16 and/or adjacent tubing, and inverting the valve assembly 16 as shown in FIG. 2. Then, housing 32 of valve assembly 16 must be tapped or struck with a finger such as shown in FIG. 3. This frees the air bubbles which have collected in the vicinity of the regulator 34 within housing 32, permitting bubbles to be carried away.

The use of a duck-bill valve in a solution administration set is quite desirable in that the valve can be inexpensively and simply manufactured, while providing very reliable performance in service. Nonetheless, the need to invert and tap the valve assembly 16 to remove air bubbles represents a significant drawback to the use of this type of valve. Not only does the inversion and tapping represent an inconvenience to the user, but more importantly, it requires a time period of approximately 24 seconds for the air bubbles to clear from the vicinity of valve assembly 16. Further, since the removal of the air bubbles requires affirmative steps on the part of the user, the possibility is raised that such steps could be inadvertently omitted, with possible adverse effects for the patient.

What is needed, therefore, is a valve assembly of the duck-bill type which provides for removal of trapped air bubbles from the valve vicinity without the need for affirmative action on the part of the user. In addition, such a valve should enable such bubbles to be removed within a time period significantly shorter than the approximately 24 seconds required for the typical valve assembly now in use. Such a valve assembly should nonetheless retain the simplicity and inexpensiveness of construction possessed by presently known valve assemblies of this type.

SUMMARY OF THE INVENTION

To overcome the aforementioned problems, the present invention provides a valve assembly for use within a flow path for permitting relatively free flow in the flow path in a first direction and for preventing flow in the path in a second, opposite direction.

A housing includes first and second ports and defines a housing interior having an interior surface. A flow regulator constructed as a single piece from a resilient material includes a pair of lips arranged in a converging relationship to define for the regulator an open end and a normally closed end. At the normally closed end, the lips are disposed adjacent each other to define a normally closed slit therebetween, and to define inner and outer surfaces for the lips. The regulator further includes at least one side wall interconnecting the lips.

Means are provided for securing the regulator within the housing interior with the normally closed end toward the second port and the open end toward the first port. Means for forming a seal between the open end of the regulator and the housing interior are also provided, so that flow in the first direction is from the first port, through the open end, through the normally closed end, and to the second port.

The housing interior defines a shape such that the regulator is secured therein by the securing means with the outer surface of each of the lips being substantially adjacent to the housing interior surface. In other words, the interior surface of the housing conforms closely to the outer surfaces of the regulator to substantially reduce the accumulation of air therebetween and facilitate clearance of air therefrom.

Accordingly, it is an object of the present invention to provide a valve assembly of the duck-bill type for use in a solution administration set in which air bubbles congregating about the valve assembly can be dislodged and carried away by a fluid stream without affirmative steps on the part of the user; to provide such a valve assembly which reduces the time required for air bubbles to be carried away; and to provide such a valve assembly which does not add any significant complexity or cost of manufacturing to such valves presently in use.

Other objects and advantages of the present invention will be apparent from the following description, the accompanying drawings, and the appended claims.

BRIEF DESCRIPTION OF THE DRAWINGS

FIG. 1 is an elevational view of a solution administration set, incorporating a valve assembly of the duck-bill type;

FIG. 2 is an elevational view of a portion of the administration set of FIG. 1, showing inversion of the valve assembly as required with valves of the prior art;

FIG. 3 is a sectional view of a valve assembly constructed according to the prior art, showing striking of the valve to dislodge air bubbles;

FIG. 4 is an exploded view of a valve assembly according to one embodiment of the present invention;

FIG. 4A is a perspective view of the regulator member of the valve assembly of FIG. 4;

FIG. 5 is a sectional view of the assembled valve shown in FIG. 4;

FIG. 6 is a sectional view of the outlet cap portion of the housing of the valve assembly of FIG. 5;

FIG. 6A is a view taken generally along the line 6A—6A of FIG. 6;

FIG. 7 is an exploded view showing another embodiment of the valve assembly of the present invention;

FIG. 8 is a sectional view showing the valve assembly of FIG. 7 in an assembled state;

FIG. 9 is a sectional view of the outlet cap portion of the housing of the valve assembly of FIG. 8;

FIG. 9A is a view taken generally along line 9A—9A of FIG. 9;

FIG. 10 is an exploded view showing a further embodiment for the valve assembly of the present invention;

FIG. 11 is a sectional view of the valve assembly of FIG. 10 in an assembled state;

FIG. 12 is a view taken generally along the line 12—12 of FIG. 11;

FIG. 13 is a view generally similar to FIG. 11, showing a variation on the valve assembly embodiment of FIG. 10;

FIG. 14 is a view taken generally along line 14—14 of FIG. 13;

FIG. 15 is an exploded view showing a still further embodiment of the valve assembly of the present invention;

FIG. 16 is a plan view of the inlet cap portion of the housing of the valve assembly of FIG. 15;

FIG. 17 is a view taken generally along line 17—17 of FIG. 16;

FIG. 18 is a view taken generally along line 18—18 of FIG. 16; and

FIG. 19 is a view showing the valve assembly of FIG. 15 mounted directly to a Y-injection site.

DETAILED DESCRIPTION OF THE PREFERRED EMBODIMENTS

Referring generally to the drawings, and in particular to FIGS. 4, 4A, 5, 6 and 6A, a valve assembly in accordance with one embodiment of the present invention is shown. A generally cylindrical housing 40 includes a cylindrical central portion 42 and an inlet cap 44 fittable within one end of central portion 42. Housing 40 is preferably formed from a transparent acryllic plastic material, although many other materials could also be used, depending upon the particular application for the valve assembly. Inlet cap 44 includes a projecting flange 46 that fits within central portion 42 to hold inlet cap 44 in place. An inlet port 48 extends outwardly from inlet cap 44, and is connectable with tubing 50 for coupling the valve assembly to the remainder of the solution administration set.

A flow regulator member 52, molded as a single piece from a material such as rubber or resilient plastic, is formed in a generally cylindrical, hollow shape. A pair of lips 54 form a portion of regulator 52 and are disposed in a converging relationship so that lips 54 are adjacent each other at one end of regulator 52, as shown in FIG. 4A. Lips 54 thus form a normally closed slit 56 to define a normally closed end for regulator 52.

A cylindrical side wall 58 interconnects lips 54 and defines an open end 60 for regulator 52. An outwardly extending flange 62 is located around open end 60.

The means for mounting regulator 52 within housing 40 can be seen from FIG. 5. A stepped surface 64 is formed within the interior of central portion 42 of housing 40, so that when regulator 52 is placed within central portion 42, flange 62 rests against stepped surface 64 to properly position regulator 52. Flange 46 of inlet cap 44 is then placed into center portion 42, with its leading edge resting against flange 62 of regulator 52. Inlet cap 44 is then secured to central portion 42 by any suitable method, such as gluing, sonic welding or the like.

An outlet cap 66 forms the end of housing 40 opposite inlet cap 44. An outlet port 68 extends outwardly from cap 66, and is connectable to tubing 70 for coupling the valve assembly to the lower portion of the solution administration set shown in FIG. 1.

Outlet cap 66 has a housing insert 72 molded integrally therewith which further defines the configuration of the interior of housing 40. A pair of projections 74 extend inwardly, with each projection 74 having an inner face 76 that define a V-shaped notch between projections 74. A slot 78 is formed at the base of the V-shaped notch, with a fluid manifold 80 being formed in the base of slot 78. Fluid manifold 80 in turn connects with outlet port 68, to direct flow from the interior of housing 40.

Housing insert 72 is formed of a general outer diameter equal to the inner diameter of central portion 42, so that outlet cap 66 is mounted to central portion 42 by placement of insert 72 within central portion 42 as shown in FIG. 5. Outlet cap 66 is then secured to central portion 42 by any suitable method, including gluing, sonic welding and the like.

As seen in FIGS. 5 and 6, the V-shaped notch formed by inner faces 76 of projections 74 is sized so that upon placement of regulator member 52 within the interior of housing 40, lips 54 of regulator 52 will fit adjacent inner faces 76 of projection 74. Thus, slit 56 is disposed within slot 78. Fluid flow into inlet port 48 thus passes through open end 60 of regulator 52 and to slit 56. The fluid pressure against the portion of lips 54 near slit 56 opens the slit, allowing the fluid to pass into the fluid manifold 80 and then through outlet port 68. Should fluid enter the valve housing 40 through outlet port 68, however, fluid pressure against the exterior surface of lips 54 will cause slit 56 to be closed, thereby preventing flow through the valve assembly in this direction.

It has been found that by modifying the configuration of the interior of housing 40, accomplished in this embodiment through use of housing inserts 72 on outlet cap 66, the problems described in the background section of the present application can be overcome. In particular, the need to invert and tap the valve assembly to clear accumulated air bubbles from the valve vicinity is eliminated, and accumulated air bubbles are removed from the valve vicinity within approximately 6.2 seconds, rather than the 24 seconds required with valves constructed according to the prior art.

While the foregoing embodiment of the present invention solves the problems of the prior art and meets the objectives of the invention, other embodiments have been found to give even better performance. One such embodiment is shown in FIGS. 7, 8, 9 and 9A, where it will be understood that similar reference numerals are used to indicate parts similar to those shown in the embodiment of FIGS. 4–6A. To distinguish between the two embodiments, however, reference numerals relating to the second embodiment have added thereto the suffix "a". It will be understood that the basic structure of the second embodiment of the valve assembly is substantially the same as that of the first embodiment, and thus only the differences therebetween will be discussed in detail.

The most significant difference can be best seen in FIGS. 7 and 8. The region of central portion 42a adjacent inlet cap 44a has been significantly shortened as has been flange 46a carried on inlet cap 44a. As seen in FIG. 8, this change eliminates the portion of the interior of housing 40a between inlet port 48a and the opening end 60a of regulator 52a. This change does not affect the means for securing regulator 52a within housing 40a, which is secured by positioning flange 62a between stepped surface 64a of central portion 42a and flange 46a.

It has been found that elimination of this region of the interior of housing 40a results in even faster clearing time for air bubbles from the vicinity of the valve assembly.

In addition, a different configuration for fluid manifold 80a opening into outlet port 68a is provided, as best seen in FIG. 9a.

A third embodiment for the valve assembly of the present invention is shown in FIGS. 10, 11 and 12. Again, similar reference numerals are used for parts corresponding to similar parts in the first and second embodiments described above, with the reference numerals for the present embodiment being distinguished by the suffix "b". The valve assembly is operatively similar to the embodiments set forth above, and thus only differences therebetween will be described in detail.

Initially, it will be noted that housing 40b and regulator 52b, while being generally similar to those of the first and second described embodiments, are generally more compact, therefore enabling the entire valve assembly to be of a smaller overall size. Accordingly, side wall 58b of regulator 52b is made sufficiently shorter so that lips 54b terminate substantially at flange 62b. The operation of regulator 52b is nonetheless the same, and the cooperation therewith and general shape of outlet cap 66b and housing insert 72b is also similar, although the specific dimensions thereof are generally smaller.

Turning now to the inlet end of the valve assembly, the inward flange from the inlet cap (shown, for example, as flange 46 from inlet cap 44 in FIG. 4) is replaced with a cylindrical insert 45b, having a projection 47b carried thereon. Insert 45b and projection 47b are appropriately sized so that insert 45b fits within the inlet end of central portion 42b, while projection 47b fits within the open end 60b of regulator 52b. Regulator 52b is secured within housing 40b by placement of flange 62b between stepped surface 64b of central portion 42b and the insert 45b.

By providing projection 47b (which extends slightly into the interior of regulator 52b), the interior of housing 40b is restricted so that it includes essentially only the interior of regulator 52b. By directing fluid from inlet port 48b directly to the interior of regulator 52b, it has been found that air bubble formation is reduced, thereby further reducing the time required air bubbles to clear from the vicinity of the valve assembly. It has been experimentally determined that this embodiment can provide clearance times of approximately 3.2 seconds.

This concept is carried further in the variation of this embodiment shown in FIGS. 13 and 14. Here, projection 47b' extends even further into regulator 52b, so that fluid from inlet port 48b enters the interior of housing 40b only a short distance from slit 56b. Thus, the effective size of the interior of housing 40b is reduced even further.

A fourth, and most preferred, embodiment of the present invention is shown in FIGS. 15, 16, 17, and 18. In this embodiment, the smaller regulator 52c of the third embodiment is used, and the central portion of the housing is eliminated so that housing 40c is formed from inlet cap 44c and outlet cap 66c.

The projection 47c which fits partially into the open end 60c of regulator 52c is carried directly on the surface of inlet cap 44c. A flange 49c extends around the outer edge of inlet cap 44c and cooperates with an annular flange 67c which extends around the edge of outlet cap 66c. Flanges 49c and 67c cooperate to close the housing 40c. A stepped surface 69c is formed along the inside of flange 67c, with regulator 52c being secured within housing 40c by placement of its flange 62c between stepped surface 69c and the surface of inlet cap 44c.

One advantage of the compact size of the valve assembly incorporating housing 40c is that it may be mounted directly to a Y-site as shown in FIG. 19. Outlet port 68c of valve assembly 90 is inserted directly into one branch 92 of Y-site 94. Alternatively, the Y-site 94 can be formed integrally with outlet cap 66c. By so doing, the number of components within a solution administration set, along with the number of coupling sites for tubing, can be reduced.

A further advantage is obtainable with the embodiments of the present invention, with the exception of that shown in FIGS. 4–6A. Referring briefly back to FIG. 1, in emergency situations it may occasionally be necessary to administer medication to a patient through the solution administration set. In such a case, a hypodermic needle and syringe may be used to inject the medication directly into Y-site 18 through the branch shown connected to filter and manual pump device 30. In such a case, relatively high fluid pressure is developed in the administration set through the injection action by the syringe. When a valve assembly of the type such as shown in FIG. 3 is used, the fluid pressure may be so great that the regulator member 34 is actually inverted and cannot operate properly as a check valve.

In any of the embodiments other than that shown in FIGS. 4–6A, the interior of the valve assembly housing does not extend to the region between the open end of regulator and the inlet port. Thus, and particularly in the embodiment shown in FIGS. 13 and 14, it is not possible for high fluid pressure to invert the regulator member, since there is no region of the housing interior into which the regulator may be inverted. Thus, this problem is eliminated.

While the forms of apparatus herein described constitute preferred embodiments of this invention, it is to be understood that the invention is not limited to these precise forms of apparatus and that changes may be made therein without departing from the scope of the invention which is defined in the appended claims.

What is claimed is:

1. Valve assembly for use within a flow path for permitting relatively free flow in said flow path in a first direction and for preventing flow in said path in a second, opposite direction, comprising:
   a housing defining a housing interior having an interior surface and having first and second ports opening into said housing;
   a flow regulator constructed as a single piece from a resilient material, said regulator including a pair of planar lips arranged in a converging relationship to define for said regulator an open end and a normally closed end whereat said lips are disposed adjacent each other to define a normally closed slit therebetween and to define inner and outer planar surfaces for said lips, said regulator further including at least one side wall interconnecting said lips;
   means for securing said regulator within said housing interior with said normally closed end toward said second port and said open end toward said first port; and
   means for forming a seal between said open end of said regulator and said housing interior so that flow in said first direction is from said first port, through said open end, through said normally closed end and to said second port;
   said housing interior defining a shape such that said regulator is secured therein by said securing means with said outer surface of each of said lips being substantially adjacent to said housing interior surface when said normally closed end of said regulator is closed; and
   said first and said second ports each having a cross-sectional area smaller than any cross-sectional area of said housing interior, said second port opening into said housing immediately adjacent said normally closed end of said regulator.

2. The valve assembly as defined in claim 1 wherein said regulator securing means and said seal means include an outward flange formed about said open end of said regulator, and wherein said housing includes a body portion and an inlet cap member mounted thereto, said cap member having inner and outer surfaces and having said first port defined therethrough, said body portion and said cap member cooperating to define an annular groove therebetween about said interior surface of said housing, said flange being fitted within said groove.

3. The valve assembly as defined in claim 2, wherein said cap member is formed so that said inner surface thereof is disposed adjacent said open end of said regulator, whereby flow from said first port passes directly through said open end.

4. The valve assembly as defined in claim 2, wherein said cap member is formed so that said inner surface thereof is disposed adjacent said open end of said regulator, said cap member including a projection carried on said inner surface thereof and extending through said open end of said regulator, said first port being further defined through said projection, whereby flow from said first port emerges directly into said regulator.

5. The valve assembly as defined in claim 1 wherein said housing includes a body portion and an outlet cap member mounted thereto, said cap member having inner and outer surfaces and having said second port defined therethrough, and wherein said cap member includes a projection carried on said inner surface within said body portion and having a distal end forming a portion of said interior surface of said housing, said projection having a V-shaped notch defined therein with the opening of said second port defined at the base of said notch, said lips of said regulator being disposed within said notch whereby said outer surface of each of said lips are thereby adjacent to said housing interior surface.

6. The valve assembly as defined in claim 1 further comprising a Y-injection site having a pair of inlet conduits and an outlet conduit, one of said inlet conduits defining said second port of said housing.

7. Valve assembly for use within a flow path for permitting relatively free flow in a first direction and for preventing flow in said path in a second, opposite direction, comprising:
   a housing defining a housing interior having an interior surface and having first and second ports opening into said housing;
   a flow regulator constructed as a single piece from a resilient material, said regulator including a pair of planar lips arranged in a converging relationship to define for said regulator an open end and a normally closed end whereat said lips are disposed adjacent each other to define a normally closed slit therebetween, said regulator further including at least one side wall interconnecting said lips, said lips and said side wall defining inner and outer planar surfaces for said regulator;
   means for securing said regulator within said housing interior with said normally closed end toward said second port and said open end toward said first port; and
   means for forming a seal between said open end of said regulator and said housing interior so that flow in said first direction is from said first port, through said open end, through said normally closed end, and to said second port;

said housing interior defining a shape and size substantially identical to the shape and size of said outer surface of said regulator such that said regulator is secured within said housing with said outer surface of said regulator adjacent said interior surface of said housing when said normally closed end of said regulator is closed; and said first and said second ports each having a cross-sectional area smaller than any cross-sectional area of said housing interior, said second port opening into said housing immediately adjacent said normally closed end of said regulator.

* * * * *